United States Patent
Troutman et al.

(10) Patent No.: US 6,967,252 B2
(45) Date of Patent: Nov. 22, 2005

(54) FLAME RETARDING COMPOUNDS

(75) Inventors: Malisa V. Troutman, New York, NY (US); Ramanathan Ravichandran, Suffern, NY (US); Redina Kote, Peekskill, NY (US); Roswell E. King, Pleasantville, NY (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 94 days.

(21) Appl. No.: 10/320,155

(22) Filed: Dec. 16, 2002

(65) Prior Publication Data

US 2003/0191213 A1 Oct. 9, 2003

Related U.S. Application Data

(60) Provisional application No. 60/342,331, filed on Dec. 21, 2001, and provisional application No. 60/416,556, filed on Oct. 7, 2002.

(51) Int. Cl.$^7$ .......................................... C07D 215/17
(52) U.S. Cl. ..................................... 546/201; 546/242
(58) Field of Search ................................. 546/201, 242

(56) References Cited

U.S. PATENT DOCUMENTS

| 5,096,950 | A | 3/1992 | Galbo et al. ............... 524/99 |
| 5,393,812 | A | 2/1995 | Haley et al. ............... 524/91 |
| 5,777,113 | A | 7/1998 | Pitteloud .................. 544/198 |
| 5,844,026 | A | 12/1998 | Galbo et al. ............. 524/100 |
| 6,117,995 | A | 9/2000 | Zedda et al. ............. 544/207 |
| 6,271,377 | B1 | 8/2001 | Galbo et al. ............. 546/14 |
| 6,309,987 | B1 | 10/2001 | Srinivasan ............... 442/147 |
| 6,441,243 | B1 | 8/2002 | Sommerlade et al. ..... 568/322 |

FOREIGN PATENT DOCUMENTS

| DE | 10113209 A1 * | 9/2001 |
| EP | 0389430 | 9/1990 |
| EP | 0792911 | 9/1997 |
| EP | 1104766 | 6/2001 |
| WO | 99/00450 | 1/1999 |

OTHER PUBLICATIONS

Mori, yukie, J Phys Chem, vol. 104, pp 4896–4905, 2000.*
Kalai, CA 131:87789, abstract of Synthesis, vol. 6, pp 973–980, 1999.*
Krishna, Murali, J Med. Chem., vol. 41, No. 18, pp 3477–3492, 1998.*

L. Dulog et al., Makromol. Chem. vol. 189, pp. 2611–2615 (1988).

R. Srinivasan et al., "A Revolutionary UV Stable Flame Retardant System for Polyolefins", Int. Conf. Addit. Polyolefins, (1998), pp. 69–83.

R. Srinivasan et al., "Advances in a Revolutionary Flame Retardant System for Polyolefins", Polyolefins 2000, Int. Conf. Polyolefins 2000, pp. 571–581.

N. Kaprinidis and R. King, an abstract posted on the Society of Plastics Engineers website, posted Sep. 2001, Abstract for paper submitted to the Polymer Modifiers and Additives Div., presented at the Polyolefins 2002 Conference on Feb. 24, 2002.

* cited by examiner

*Primary Examiner*—D. Margaret Seaman
(74) *Attorney, Agent, or Firm*—Tyler A. Stevenson

(57) ABSTRACT

Novel flame retarding compounds that comprise at least one sterically hindered nitroxyl, hydroxylamine or hydrocarbyloxyamine moiety and at least one conventional organohalogen or organophosphorus flame retardant moiety, represented by $$(HA)_x - (L)_y - (FRM)_z$$

where

HA is independently of each other a sterically hindered nitroxyl, sterically hindered hydroxylamine or sterically hindered hydrocarbyloxyamine moiety, L is independently of each other a direct bond or chemical linking group, FRM is independently of each other an organohalogen or an organophosphorus flame reatardant moiety, and x, y and z are each independently greater than or equal to 1, are especially effective towards providing flame retardancy to organic polymer substrates.

5 Claims, No Drawings

FLAME RETARDING COMPOUNDS

This application claims the benefit under 35 USC 119(e) of U.S. provisional application Nos. 60/342,331, filed Dec. 21, 2001 and 60/416,556, filed Oct. 7, 2002.

The instant invention pertains to novel flame retarding compounds that comprise at least one sterically hindered nitroxyl, hydroxylamine, hydrocarbyloxyamine moiety and at least one conventional organohalogen or organophosphorus flame retardant moiety.

BACKGROUND OF THE INVENTION

U.S. Pat. No. 5,096,950 discloses the co-use of certain NOR (N-alkoxy) hindered amines with a brominated $Sb_2O_3$-containing flame retardant in polypropylene.

U.S. Pat. No. 5,393,812 discloses polyolefin compositions which are made flame retardant by a combination of a halogenated hydrocarbyl phosphate or phosphonate ester flame retardant in combination with a alkoxyamine functional hindered amine.

U.S. Pat. No. 5,844,026 discloses polyolefin compositions comprising certain NOR hindered amines and certain conventional flame retardants.

U.S. Pat. No. 6,117,995 discloses that certain N-alkoxy hindered amines may be used as flame retardants for organic polymers.

U.S. Pat. No. 6,271,377 discloses polyolefin compositions that comprise N-hydroxyalkoxy hindered amines and a halogenated flame retardant.

U.S. Pat. No. 6,309,987 and equivalent WO 99/54530 teach polyolefin non-woven flame retardant fabrics that comprise N-alkoxyamines.

A Revolutionary UV Stable Flame Retardant System for Polyolefins—R. Srinivasan, A. Gupta and D. Horsey, *Int. Conf. Addit. Polyolefins* 1998, 69–83, teaches polyolefins comprising certain NOR hindered amines with halogen and phosphorus containing conventional flame retardants.

Advances in a Revolutionary Flame Retardant System for Polyolefins—R. Srinivasan, B. Rotzinger, *Polyolefins 2000, Int. Conf Polyolefins* 2000, 571–581, teaches polyolefins comprising certain NOR hindered amines with brominated and phosphorus containing flame retardants.

N. Kaprinidis and R. King, in an abstract posted on the Society of Plastics Engineers website, posted September 2001, discuss the use of NOR hindered amines as flame retardants in polyolefins. The abstract is for a paper submitted to the Polymer Modifiers and Additives Division subsection to be presented at the Polyolefins 2002 conference in Houston, Tex., Feb. 24, 2002. The website is www.PMAD.org.

EP 0792911 A2, discloses polyolefin compositions that comprise alkoxyamine functional hindered amines and tris (trihalogenopentyl) phosphate flame retardants.

WO 99/00450, copending U.S. application Nos. 09/502, 239, filed Nov. 3, 1999, and 09/714,717, filed Nov. 16, 2000, disclose the use of certain N-alkoxy hindered amines as flame retardants.

EP 1104766 discloses cross-linked phenoxyphosphazene compounds as flame retardants for synthetic resins.

The flame retardant (FR) market today is comprised of products which function to interfere with the combustion process by chemical and/or physical means. Mechanistically these FRs have been proposed to function during combustion of an article in either the gas phase, the condensed phase or both. The organohalogens are proposed to generate halogen species (e.g. HX) which interferes in the gas phase with free radical organic "fuel" from the polymer substrate. Synergists are proposed to react with HX to form additional chemical species which interfere with combustion in the gas phase, such as reaction of antimony oxide with HX to form antimony halide and water vapor. Antimony compounds such as antimony trioxide also act as radical scavengers forming antimony halides. Thus, they can inhibit the propagation of the fire.

Although antimony compounds are efficient in terms of cost performance, they recently raised concern because of the toxicity of the byproducts which are formed during combustion in the presence of a halogenated flame retardant. Antimony oxides often contain trace amounts of arsenic compounds which are suspected carcinogens. Because of these ecological concerns, there is a movement to replace antimony trioxide in the present commercial flame retardant applications. However, it is very difficult to find an effective synergist which is both environmentally friendly and efficient as far as cost performance is concerned.

Another reason to add flame retardant additives is to prevent dripping during the application of the fire. During combustion, parts of the polymer separate from the matrix in the shape of droplets. Often, the droplets are flaming and impose tremendous danger for fire spread. It is common to add fillers such as talc in large amounts to the polymer, with negative consequences on the mechanical properties. Other fillers sometimes used include calcium carbonate, magnesium carbonate, zinc borate, silicates, silicones, glass fibres, glass bulbs, asbestos, kaolin, mica, barium sulfate, calcium sulfate, metal oxides, hydrates and hydroxides such as zinc oxide, magnesium hydroxide, alumina trihydrate, silica, calcium silicate, magnesium silicate.

It has been found that polymers with good flame retardant properties are prepared when novel compounds are added that comprise at least one sterically hindered nitroxyl, hydroxylamine or hydrocarbyloxyamine moiety and at least one conventional organohalogen or organophosphorus flame retardant moiety. With the use of these novel compounds, antimony compounds and fillers may be largely reduced or replaced. As the instant compounds are active as stabilizers, the polymer compositions of the invention are efficiently protected from the deleterious effects of light, oxygen and/or heat.

DETAILED DISCLOSURE

The instant invention pertains to novel flame retardant compounds that comprise at least one sterically hindered nitroxyl, hydroxylamine or hydrocarbyloxyamine moiety and at least one conventional organohalogen or organophosphorus flame retardant moiety.

The present compounds are of the formula

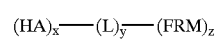

$(HA)_x\text{——}(L)_y\text{——}(FRM)_z$ where

HA is independently of each other a sterically hindered nitroxyl, sterically hindered hydroxylamine or sterically hindered hydrocarbyloxyamine moiety, L is independently of each other a direct bond or chemical linking group, FRM is independently of each other an organohalogen or an organophosphorus flame reatardant moiety, and x, y and z are each independently greater than or equal to 1.

The present compounds that comprise at least one sterically hindered nitroxyl, hydroxylamine or hydrocarbyloxyamine moiety and at least one conventional organohalogen or organophosphorus flame retardant moiety are for example represented by formula I

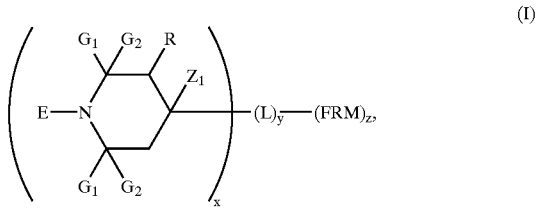

and the present compounds that comprise at least one sterically hindered hydrocarbyloxyamine moiety and at least one conventional organohalogen or oganophosphorus moiety are further represented for example by formulae II and III

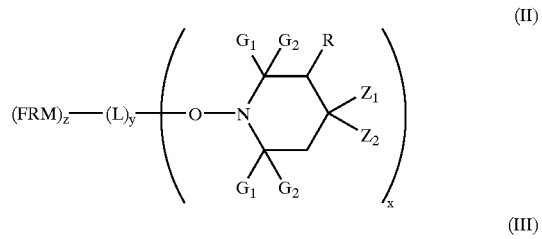

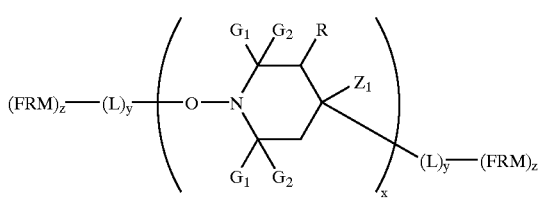

where in formulae I, II and III
R is hydrogen or methyl,
$G_1$ and $G_2$ are independently alkyl of 1 to 4 carbon atoms or are together pentamethylene,
x, y and z are each independently greater than or equal to 1,
L is independently of each other a direct bond or a chemical linking group,
$Z_1$ and $Z_2$ are independently hydrogen or hydrocarbyl, or together form a hydrocarbylene group, or are independently $-OR_1$, $-OCOR_1$, $-COOR_1$, $-CONR_1R_2$, $-NR_1COR_2$, $-COR_1$ or $-NR_1R_2$,
$R_1$ and $R_2$ are independently of each other hydrogen or hydrocarbyl, or $R_1$ and $R_2$ together form a hydrocarbylene group,
E is oxyl, hydroxyl, alkoxy, cycloalkoxy, aralkoxy, aryloxy, $-O-CO-OG$, $-O-Si(G)_3$, or $-O-CH_2-OG$ where G is selected from the group consisting of hydrogen, an aliphatic, araliphatic and aromatic moiety; or E is $-O-T-(OH)_b$,
T is a straight or branched chain alkylene of 1 to 18 carbon atoms, cycloalkylene of 5 to 18 carbon atoms, cycloalkenylene of 5 to 18 carbon atoms, a straight or branched chain alkylene of 1 to 4 carbon atoms substituted by phenyl or by phenyl substituted by one or two alkyl groups of 1 to 4 carbon atoms, b is 1, 2 or 3 with the proviso that b cannot exceed the number of carbon atoms in T, and when b is 2 or 3, each hydroxyl group is attached to a different carbon atoms of T, and FRM is independently of each other an organohalogen or an organophosphorus flame retardant moiety.

E is for example oxyl, hydroxyl, alkoxy, cycloalkoxy or aralkoxy. For instance, E is methoxy, propoxy, cyclohexyloxy or octyloxy.

The terms x, y and z independently may be for example 1 to about 200, 1 to about 100, 1 to about 50, for instance 1 to about 25, 1 to about 10 or 1 to about 5, for example, each may be independently 1, 2, 3, 4 or 5.

The term "hydrocarbyl group" broadly refers to a monovalent hydrocarbon group in which the valency is derived by abstraction of a hydrogen from a carbon atom. Hydrocarbyl includes for example aliphatics (straight and branched chain), cycloaliphatics, aromatics and mixed groups such as aralkyl, alkylaryl, alkynyl, cycloalkynyl. Hydrocarbyl includes such groups as alkyl, cycloalkyl, aryl, aralkyl, alkylaryl, alkenyl, and cycloalkenyl. A hydrocarbyl may optionally be interrupted by carbonyl, carboxyl, amino, amido, thio, sulfoxide, sulfonyl and ether groups and/or may optionally be substituted by hydroxy, amino, amido, carboxyl and thio groups.

The term "hydrocarbylene" broadly refers to any divalent hydrocarbon in which both valencies derive by abstraction of hydrogens from carbon atoms. Included within the definition of hydrocarbylene are the same groups as indicated herein for hydrocarbyl, with of course, the extra valency, for example alkylene, alkenylene, arylene, alkylaryl, etc.

For the purposes of this invention, and as is understood in the art, the term "moiety" means a chemical functional group when it is part of a larger compound, for example when part of a compound of formula I, II or III. For example, the term "organohalogen or organophosphorus flame retardant moiety" refers to the conventional organic flame retardant portion(s) of the compounds of formulae I, II and III. Likewise the term "hindered hydrocarbyloxyamine moiety" refers to the portion of formulae I, II and III with hydrocarbyloxyamine additive functionality. For the purposes of this invention, the term moiety is not limited to a single active functionality. For example, a chemical group containing two (or more) hindered amine groups may be considered a single moiety.

Alkyl is a straight or branched chain of for example 1 to 24 carbon atoms, for instance, 1 to 18 carbon atoms or 1 to 12 carbon atoms, and is for example methyl, ethyl, n-propyl, n-butyl, sec-butyl, tert-butyl, n-hexyl, n-octyl, 2-ethylhexyl, n-nonyl, n-decyl, n-undecyl, n-dodecyl, n-tridecyl, n-tetradecyl, n-hexadecyl or n-octadecyl.

Cycloalkyl groups are for example of from 5 to 7 carbon atoms and include cyclopentyl and cyclohexyl; typical cycloalkenyl groups include cyclohexenyl.

Aralkyl groups are for example of 7 to 9 carbon atoms and include benzyl, alpha-methyl-benzyl, alpha,alpha-dimethylbenzyl or phenethyl.

Aryl is for instance phenyl, napthyl and biphenyl.

Alkoxy and aryloxy groups are defined as for the present alkyl and aryl groups.

Halogen is for instance chloro and bromo.

The compounds of the present invention do not have any peroxy linkages. Likewise, the only possible N—O bond is in the HA moieties (in which it is necessary).

Chemical Linking Groups L

The chemical linking groups L may for example be any divalent or polyvalent linking group. Linking groups L are for example esters, amides, and other common divalent or polyvalent groups, for example —OCO—, —COO—, —O—, —CONR$_1$—, —NR$_1$CO—, —CO—, —NR$_1$—, —S—$_1$, —SO—, SO$_2$—, —CSO—, —COS—, —CSS—, triazinyl, and the like.

R$_1$ is independently of each other hydrogen or a hydrocarbyl group.

Polyvalent is for example trivalent and tetravalent or greater. Triazinyl is a trivalent linking group.

Linking groups L may be a divalent hydrocarbylene group or polyvalent group that comprises one or more of the above ester, amide, etc., groups. The linking groups L may be terminated, interrupted or substituted by said groups.

The linking groups L may be a polymeric backbone, for example a polyamine, a polyglycol, a polyester or a polyamine/polytriazine polymer or oligomer. In this instance L is polyvalent.

A polymeric backbone (polyvalent backbone) defined herein may be for example any polymeric or oligomeric backbone known in the art as part of polymeric or oligomeric polymer additives. For example triazine-containing polymeric backbones that are part of commercial hindered amine compounds, for example Chimassorb® 944, CAS #71878-19-8. Other suitable polyvalent backbones that may define the linking group L are as in the commercial products:

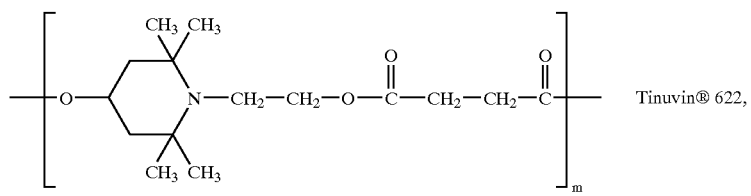

Tinuvin® 622,

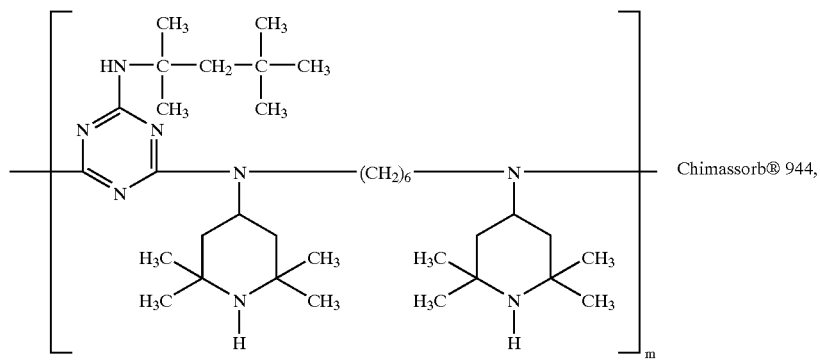

Chimassorb® 944,

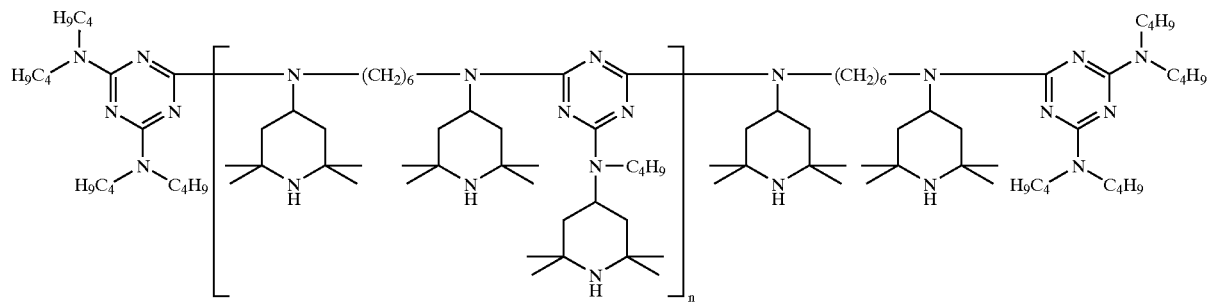

Chimassorb® 2020,

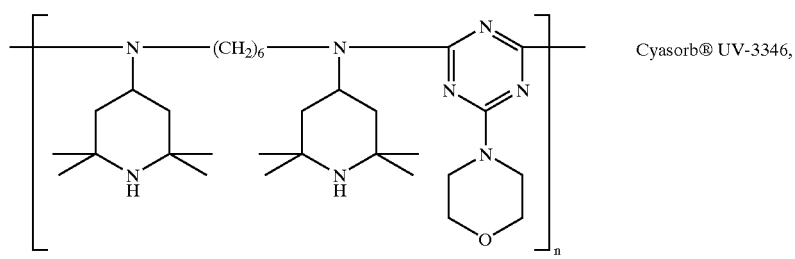

Cyasorb® UV-3346,

-continued
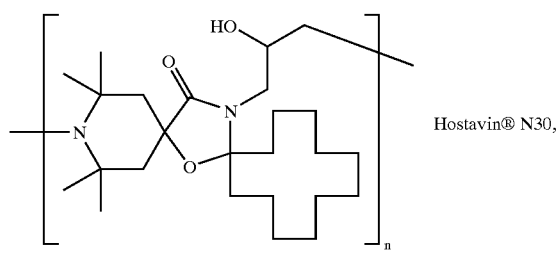 Hostavin® N30,
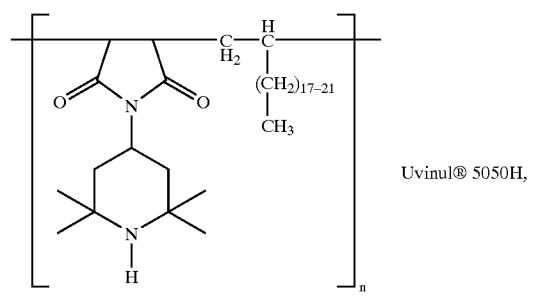 Uvinul® 5050H,
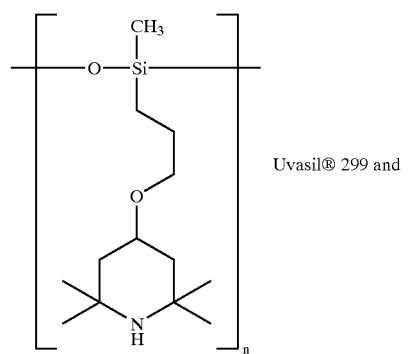 Uvasil® 299 and
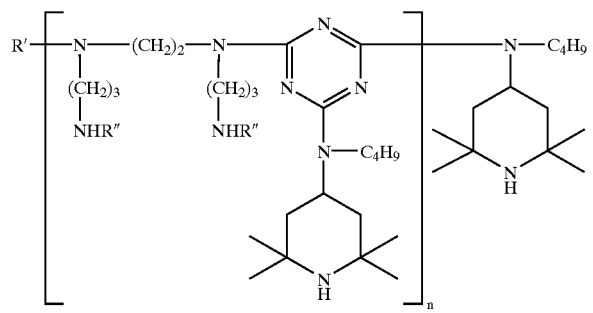

where R'=R" or H

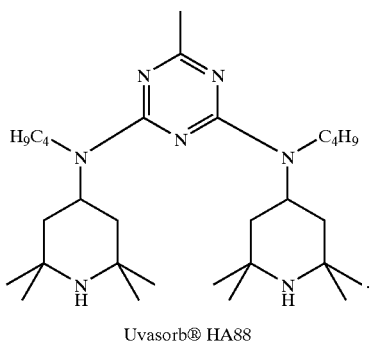

Uvasorb® HA88 and where R"=

The polymeric backbone linking groups of the present invention may be derived from known polymerization methods, for example condensation polymerization or free radical polymerization of ethylenically unsaturated monomers. Certain of known organohalogen and organophosphorus flame retardants comprise ethylenically unsaturated groups which may be co-polymerized with present sterically hindered nitroxyl, hydroxylamine and hydrocarbyloxyamine compounds that likewise comprise ethylenically unsaturated groups.

Examples of flame retardant moieties that comprise ethylenically unsaturated groups are for example

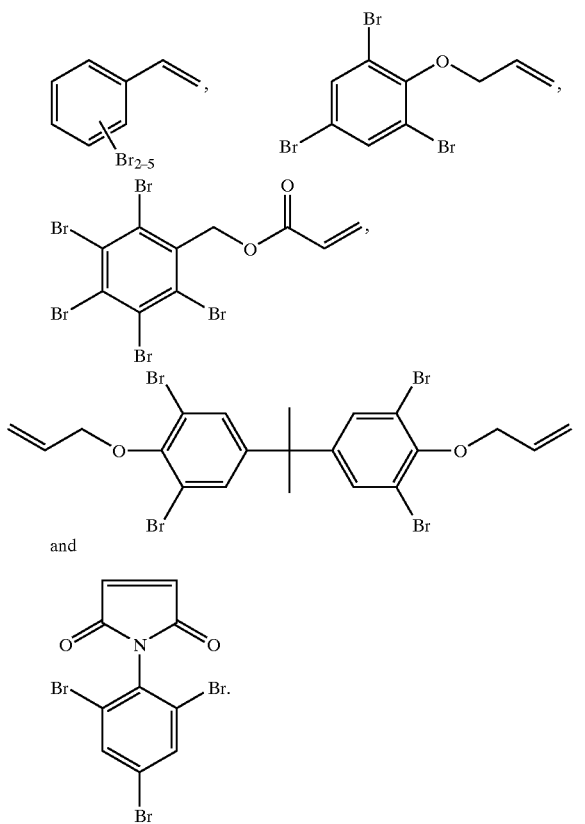

and

Examples of flame retardant moieties suitable for condensation polymerization, as a method of bonding one or more of them to a present sterically hindered nitroxyl, hydroxylamine or hydrocarbyloxyamine moiety, are for example

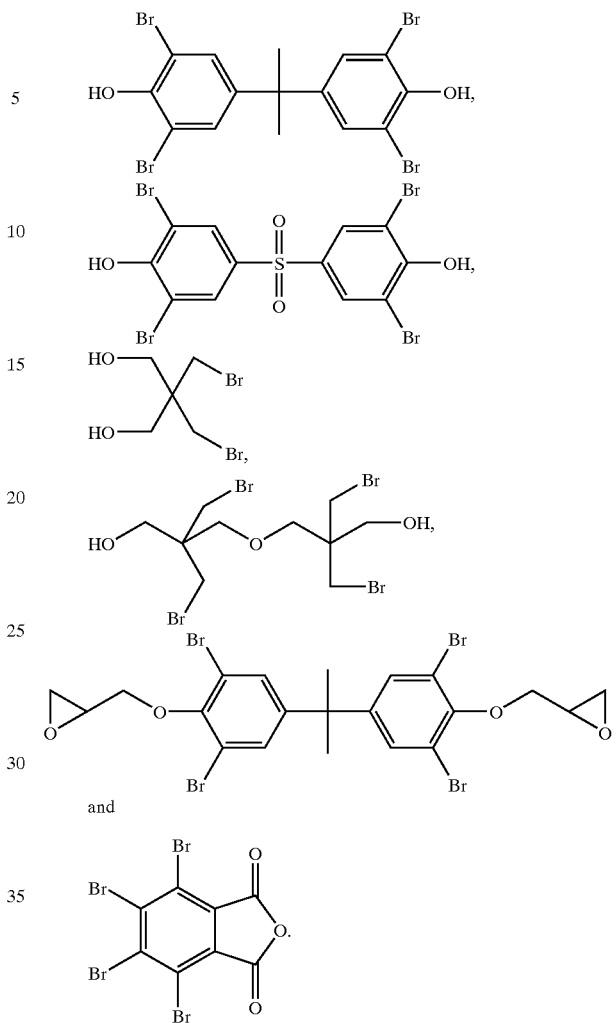

and

Other suitable polyvalent backbones are as in the compounds:

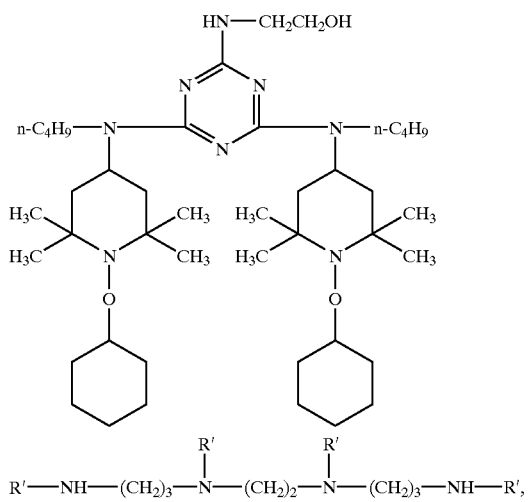

Chimassorb® 119 where R' is

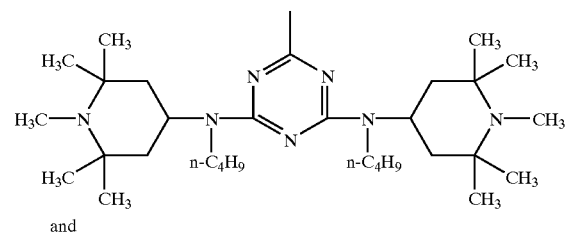

and

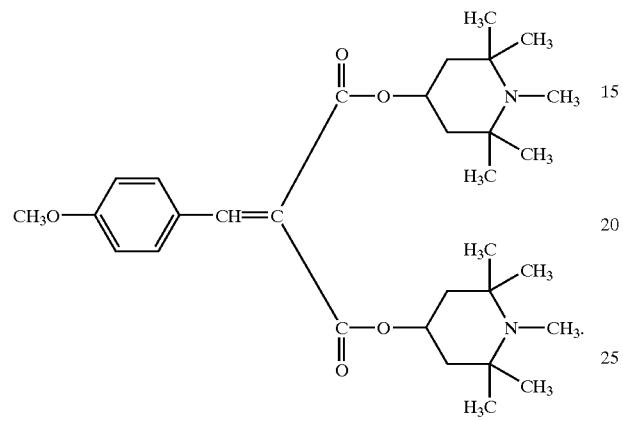

Sanduvor® PR-31

Tinuvin® and Chimassorb® are protected trade names of Ciba Specialty Chemicals Corp. Sanduvor® and Hostavin® are protected trade names of Clariant. Cyasorb® is a protected trade name of Cytec Corporation. Uvinul® is a protected trade name of BASF. Uvasil® is a protected trade name of Enichem. Uvasorb® is a protected trade name of 3V Sigma.

Organohalogen and Organophosphorus Flame Retardant Moieties (FRM)

The present FRM moieties are for example a hydrocarbyl group substituted by multiple halogen atoms, for example alkyl of 1 to 18 carbon atoms substituted by 1 to 37 bromine or chlorine atoms, cycloalkyl of 5 to 12 carbon atoms substituted by 1 to 23 bromine or chlorine atoms, aralkyl of 7 to 15 carbon atoms substituted by 1 to 5 bromine or chlorine atoms, or aryl of 6 to 12 carbon atoms substituted by 5 to 9 bromine or chlorine atoms.

For example the FRM moieties are hydrocarbyl groups substituted by 3, 4, 5, 6, 7, or 8 chlorine or bromine atoms.

The present FRM moieties are for example:

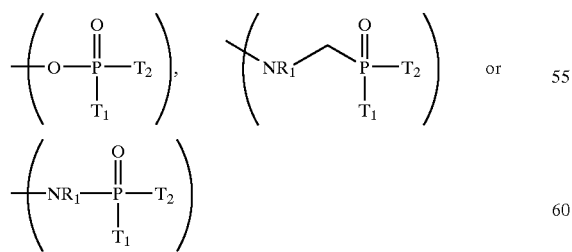

wherein $T_1$ and $T_2$ are independently alkyl, aryl, alkoxy, aralkoxy or dialkylamino; or said alkyl, aryl, alkoxy, aralkoxy or dialkylamino substituted by 1 to 8 halogen atoms, $R_1$ is defined as above;

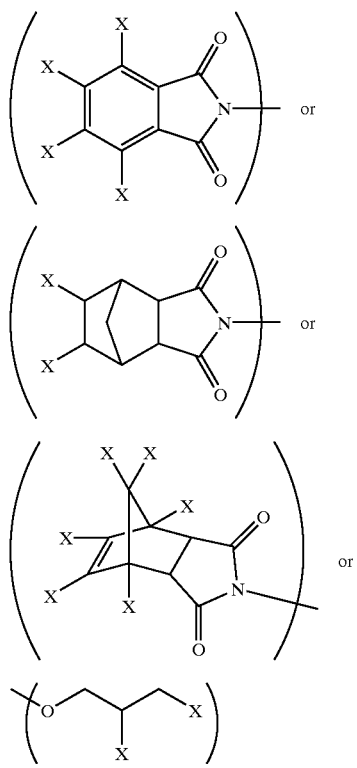

where X is chlorine or bromine;

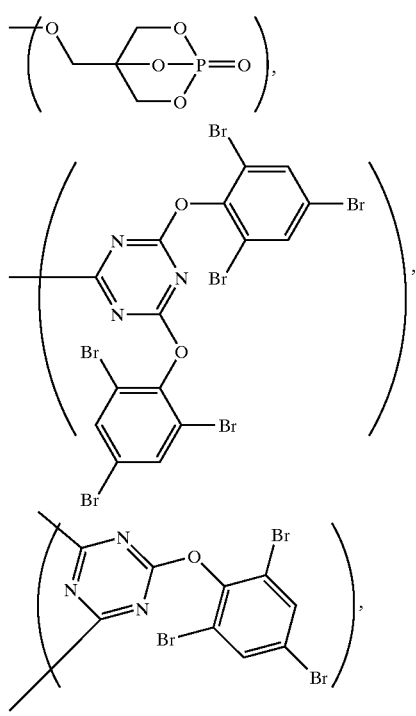

where one of the open bonds may be bonded to $T_1$, defined above,

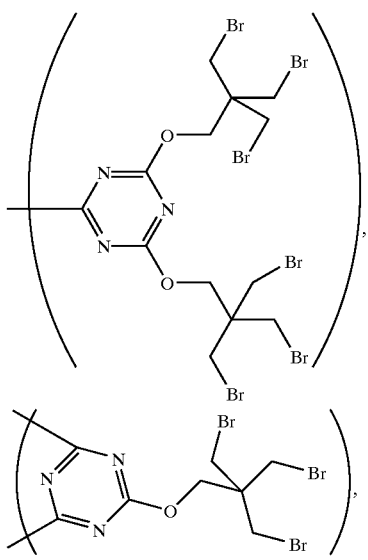

where one of the open bonds may be bonded to $T_1$, defined above,

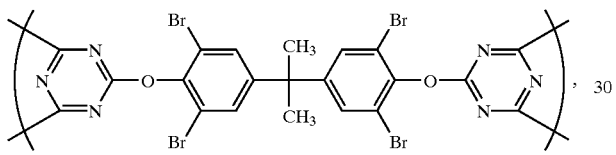

where one to three of the open bonds may be bonded to $T_1$, defined above,

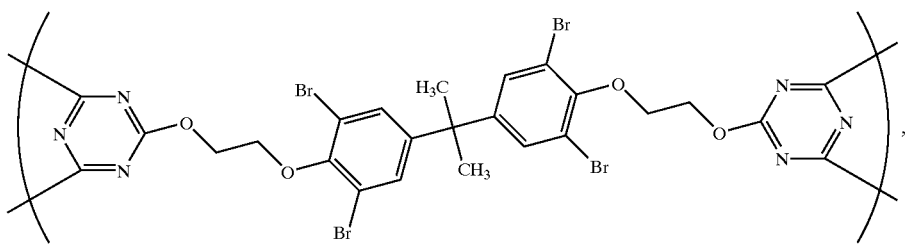

where one to three of the open bonds may be bonded to $T_1$, defined above,

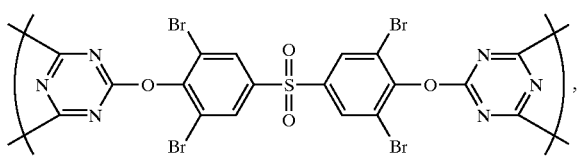

where one to three of the open bonds may be bonded to $T_1$, defined above,

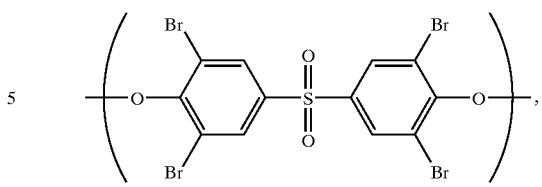

where one of the open bonds may be bound to alkyl or aryl; or said alkyl or aryl substituted by 1 to 8 halogen atoms,

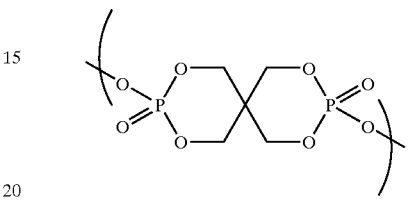

where one of the open bonds may be bound to alkyl or aryl; or said alkyl or aryl substituted by 1 to 8 halogen atoms,

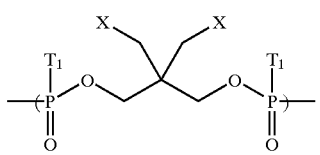

where X is chlorine or bromine; and where one of the open bonds may be bonded to $T_1$, defined above,
or
—(phosphazene flame retardant)

The phosphazene flame retardants of component are well known in the art. They are disclosed for example in EP1104766, JP07292233, DE19828541, DE1988536, JP11263885, U.S. Pat. Nos. 4,107,108, 4,108,805 and 4,079,035 and 6,265,599. The relevant disclosures of the U.S. Patents are hereby incorporated by reference.

The FRM moieties are for example based on well known commercial organohalogen, organophosphorus and melamine based flame retardants. The term "based on" means potentially derived directly from or having the same active structure less the requisite number of valencies.

Oganohalogen flame retardants are for example:
Chloroalkyl phosphate esters (ANTIBLAZE® AB-100, Albright & Wilson; FYROL® FR-2, Akzo Nobel),
polybrominated diphenyl oxide (DE-60F, Great Lakes Corp.),
decabromodiphenyl oxide (DBDPO; SAYTEX® 102E),
tris[3-bromo-2,2-bis(bromomethyl)propyl] phosphate (PB 370®, FMC Corp.), bis(2,3-dibromopropyl ether) of bisphenol A (PE68),
brominated epoxy resin,
ethylene-bis(tetrabromophthalimide) (SAYTEX® BT-93),
bis(hexachlorocyclopentadieno)cyclooctane (DECLORANE PLUS®),
chlorinated paraffins,
1,2-bis(tribromophenoxy)ethane (FF680),
tetrabromo-bisphenol A (SAYTEX® RB100),
ethylene bis-(dibromo-norbornanedicarboximide) (SAYTEX®BN-451),
bis-(hexachlorocyclopentadieno) cyclooctane,
tris-(2,3-dibromopropyl)-isocyanurate, and
ethylene-bis-tetrabromophthalimide.

The organophophorus flame retardants are for example:
Tetraphenyl resorcinol diphosphite (FYROLFLEX® RDP, Akzo Nobel),
triphenyl phosphate,
ammonium polyphosphate (APP) or (HOSTAFLAM® AP750),
resorcinol diphosphate oligomer (RDP),
phosphazene flame retardants and
ethylenediamine diphosphate (EDAP).

Melamine based flame retardants are for example:
melamine cyanurate, MELAPUR® MC,
melamine borate,
melamine phosphate, MELAPUR® P 46,
melamine polyphosphate MELAPUR® 200 and
melamine pyrophosphate.

The halogenated flame retardants useful in the present invention may be selected from organic aromatic halogenated compounds such as halogenated benzenes, biphenyls, phenols, ethers or esters thereof, bisphenols, diphenyloxides, aromatic carboxylic acids or polyacids, anhydrides, amides or imides thereof; organic cycloaliphatic or polycycloaliphatic halogenated compounds; and organic aliphatic halogenated compounds such as halogenated paraffins, oligo- or polymers, alkylphosphates or alkylisocyanurates. These components are largely known in the art, see e.g. U.S. Pat. Nos. 4,579,906 (e.g. col. 3, lines 30–41), 5,393,812; see also Plastics Additives Handbook, Ed. by H. Zweifel, 5$^{th}$ Ed., Hanser Publ., Munich 2001, pp. 681–698.

Sterically Hindered Nitroxyl, Hydroxylamine and Hydrocarbyloxyamine Moieties (HA)

The HA moieties are for example based on well known commercial hindered nitroxyl, hydroxylamine and hydrocarbyloxyamine stabilizers. The term "based on" means potentially derived directly from or having the same active structure less the requisite number of valencies.

Hindered hydrocarbyloxyamine stabilizers are well known in the art, also known as N-alkoxy hindered amines and NOR hindered amines or NOR hindered amine light stabilizers or NOR HALS.

They are disclosed for example in U.S. Pat. Nos. 5,004,770, 5,204,473, 5,096,950, 5,300,544, 5,112,890, 5,124,378, 5,145,893, 5,216,156, 5,844,026, 6,117,995, 6,271,377, and U.S. application Ser. Nos. 09/505,529, filed Feb. 17, 2000, 09/794,710, filed Feb. 27, 2001, 09/714,717, filed Nov. 16, 2000, 09/502,239, filed Nov. 3, 1999 and 60/312,517, filed Aug. 15, 2001. The relevant disclosures of these patents and applications are hereby incorporated by reference.

U.S. Pat. No. 6,271,377, and U.S. application Ser. Nos. 09/505,529, filed Feb. 17, 2000, and 09/794,710, filed Feb. 27, 2001, cited above disclose hindered hydroxyalkoxyamine stabilizers. For the purposes of this invention, the hindered hydroxyalkoxyamine stabilizers are considered a subset of the hindered hydrocarbyloxyamine stabilizers. Hindered hydroxyalkoxyamine stabilizers are also known as N-hydroxyalkoxy hindered amines, or NORol HALS.

Typical hindered nitroxyls include bis(1-oxyl-2,2,6,6-tetramethylpiperidin-4-yl) sebacate, 4-hydroxy-1-oxyl-2,2,6,6-tetramethylpiperidine, 4-ethoxy-1-oxyl-2,2,6,6-tetramethylpiperidine, 4-propoxy-1-oxyl-2,2,6,6-tetramethylpiperidine, 4-acetamido-1-oxyl-2,2,6,6-tetramethylpiperidine, 1-oxyl-2,2,6,6-tetramethylpiperidine, 1-oxyl-2,2,6,6-tetramethylpiperidin-4-one, 1-oxyl-2,2,6,6-tetramethylpiperidin-4-yl acetate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl 4-t-butyl-benzoate, bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethylpiperidin-4-yl) n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6-tetramethylpiperidin-4-yl) hexahydroterephthalate, N,N'-bis (1-oxyl-2,2,6,6-tetramethylpiperidin-4-yl)adipamide, N-(1-oxyl-2,2,6,6-tetramethylpiperidin-4-yl)caprolactam, N-(1-oxyl-2,2,6,6-tetramethylpiperidin-4-yl) dodecylsuccinimide, 2,4,6-tris-[N-butyl-N-(1-oxyl-2,2,6,6-tetramethylpiperidin-4-yl)]-s-triazine, 4,4'-ethylenebis(1-oxyl-2,2,6,6-tetramethylpiperazin-3-one), 2-oxyl-1,1,3,3-tetramethyl-2-isobenzazole, 1-oxyl-2,2,5,5-tetramethylpyrrolidine, and N,N-bis-(1,1,3,3-tetramethylbutyl)nitroxide.

Nitroxyl stabilizers are for example bis(1-oxyl-2,2,6,6-tetramethylpiperidin-4-yl) sebacate, 4-hydroxy-1-oxyl-2,2,6,6-tetramethylpiperidine, 4-ethoxy-1-oxyl-2,2,6,6-tetramethylpiperidine, 4-propoxy-1-oxyl-2,2,6,6-tetramethylpiperidine, 4-acetamido-1-oxyl-2,2,6,6-tetramethylpiperidine, 1-oxyl-2,2,6,6-tetramethylpiperidine, and 1-oxyl-2,2,6,6-tetramethylpiperidin-4-one.

A specific embodiment is where the nitroxyl stabilizers are bis(1-oxyl-2,2,6,6-tetramethylpiperidin-4-yl) sebacate and 4-hydroxy-1-oxyl-2,2,6,6-tetramethylpiperidine.

Hydroxylamine stabilizers are for example those disclosed in U.S. Pat. Nos. 4,590,231, 4,668,721, 4,691,015, 4,831,134, 5,006,577, and 5,064,883, the relevant parts of which are incorporated herein by reference.

Specific examples of suitable compounds that the present HA moieties may be based on include:

(a) the reaction product of 2,4-bis[(1-cyclohexyloxy-2,2,6,6-piperidin-4-yl)butylamino]-6-chloro-s-triazine with N,N'-bis(3-aminopropyl)ethylenediamine) [CAS Reg. No. 191680-81-6];

(b) 1-cyclohexyloxy-2,2,6,6-tetramethyl-4-octadecylaminopiperidine;

(c) bis(1-octyloxy-2,2,6,6-tetramethylpiperidin-4-yl) sebacate;

(d) 2,4-bis[(1-cyclohexyloxy-2,2,6,6-tetramethylpiperidin-4-yl)butylamino]-6-(2-hydroxyethylamino-s-triazine;

(e) bis(1-cyclohexyloxy-2,2,6,6-tetramethylpiperidin-4-yl) adipate;

(h) 2,4-bis[(1-cyclohexyloxy-2,2,6,6-piperidin-4-yl)butylamino]-6-choro-s-triazine;

(i) 1-(2-hydroxy-2-methylpropoxy)-4-hydroxy-2,2,6,6-tetramethylpiperidine;

(j) 1-(2-hydroxy-2-methylpropoxy)-4-oxo-2,2,6,6-tetramethylpiperidine;

(k) 1-(2-hydroxy-2-methylpropoxy)-4-octadecanoyloxy-2,2,6,6-tetramethylpiperidine;

(l) bis(1-(2-hydroxy-2-methylpropoxy)-2,2,6,6-tetramethylpiperidin-4-yl) sebacate;

(m) bis(1-(2-hydroxy-2-methylpropoxy)-2,2,6,6-tetramethylpiperidin-4-yl) adipate;

(n) 2,4-bis{N-[1-(2-hydroxy-2-methylpropoxy)-2,2,6,6-tetramethylpiperidin-4-yl]-N-butyl-amino}-6-(2-hydroxyethylamino)-s-triazine; and (o) the compound of formula

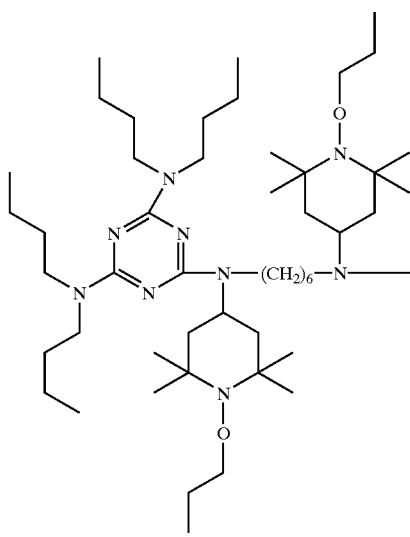
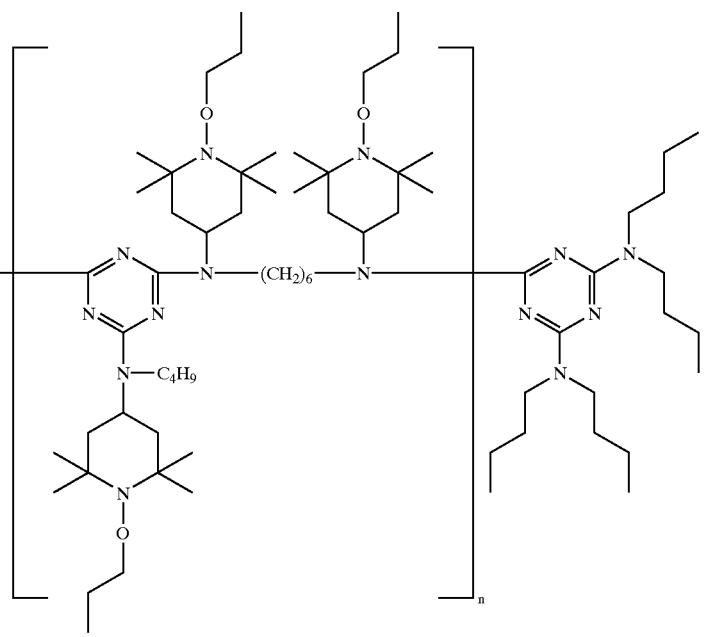

in which n is from 1 to 15.

Compound (o) is disclosed in example 2 of U.S. Pat. No. 6,117,995.

It is apparent to those skilled in the art that there is potentially significant overlap between the definition of the HA moieties and the linking groups L. That is, these groups are not mutually exclusive; in one compound the HA moiety and the L groups may be defined in more than one way and still correctly be described by formula I, II and III.

The sterically hindered nitroxyl, hydroxylamine or hydrocarbyloxyamine moiety is for example selected from the group consisting of

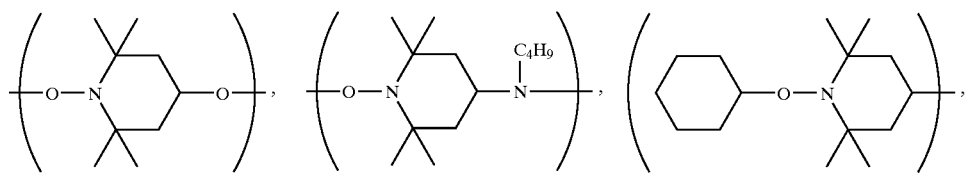

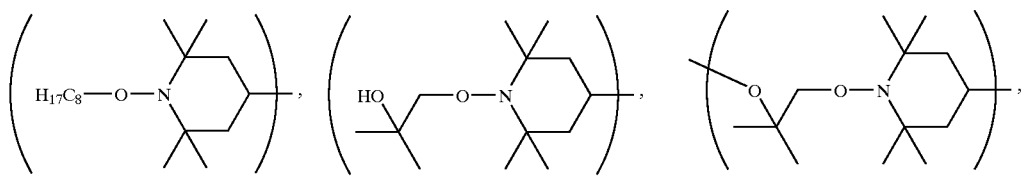

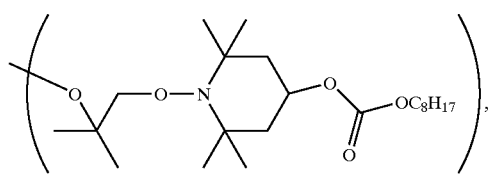

-continued

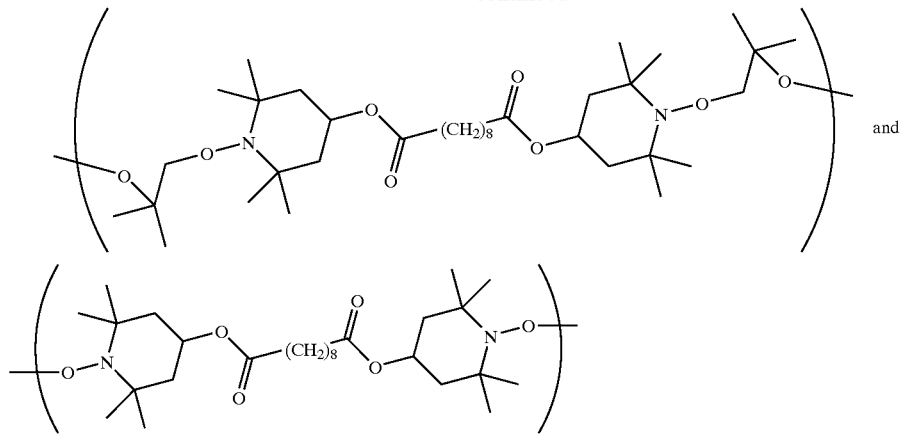

and the corresponding nitroxyl and hydroxylamine moieties where appropriate.

The present novel flame retardant compounds are advantageously employed in organic polymer substrates. As the instant nitroxyl, hydroxylamine and hydrocarbyloxyamine compounds are active as stabilizers, the polymer compositions of the invention are efficiently protected from the deleterious effects of light, oxygen and/or heat, as well as being imparted with flame retardancy.

Accordingly, the present invention also pertains to a flame retardant composition which comprises
 (A) an organic polymer substrate and
 (B) an effective flame retarding amount of at least one compound of the formula

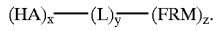

Advantageously, the compositions of the invention may further contain a conventional flame retardant not bound to a hindered amine moiety, for example at least one compound selected from the group consisting of the organohalogen and the organophosphorus flame retardants. The conventional flame retardants are as described above.

Components A and B and optional further components may comprise one or a mixture of more than one chemical species.

Advantageously, present composition contains only minor amounts of antimony compounds such as $Sb_2O_3$, e.g. less than about 1%, for instance less than about 0.1% by weight of the polymer component A; for example, the present compositions are essentially free of antimony.

Flame-retardant fillers are not required in order to improve the flame retardant properties and achieve a higher rating, e.g. in the UL-94 burning test (infra). Consequently, the compositions of the present invention may contain only minor amounts of flame-retardant fillers, e.g. less than about 3%, for instance less than about 1%, for example less than about 0.1% by weight of the polymer component A; for example, the present compositions are essentially free of flame-retardant fillers.

Flame-retardant fillers are known in the art and are selected from the group consisting of magnesium hydroxide, alumina trihydrate and zinc borate. Flame-retardant fillers are inorganic compounds employed for flame-retardant properties, and at high enough levels to be considered "filler".

If conventional fillers such as talc, calcium carbonate and the like are normally employed for instance for flow properties in order to reduce the spread of flaming droplets (not flame-retardant per se), such conventional fillers may also be reduced with the use of the present compositions. For instance, the present compositions may contain only minor amounts of conventional fillers, for example less than about 3%, for instance less than 1%, for example less than about 0.1% by weight of the polymer component A; for example, the present compositions are essentially free of conventional fillers.

Further, the present invention allows for conventional fillers to take the place of more expensive flame-retardant fillers.

The polymeric substrate of component A is any of a wide variety of polymeric types including polyolefins, polystyrenics, and PVC. For example, the polymer substrate may be selected from the group of resins consisting of the polyolefins, the thermoplastic olefins, styrenic polymers and copolymers, ABS and polymers which contain hetero atoms, double bonds or aromatic rings. Specific embodiments are where component A is polypropylene, polyethylene, thermoplastic olefin (TPO), ABS or high impact polystyrene.

For example, the polymer substrate is selected from the group of resins consisting of the polyolefins, the thermoplastic olefins, styrenic polymers and copolymers, and ABS.

Another embodiment of the present invention is where the polymer substrate is selected from the group consisting of polypropylene, polyethylene, thermoplastic olefin (TPO), ABS and high impact polystyrene.

For instance, the polymer substrate is polypropylene, polyethylene or thermoplastic olefin (TPO). Organic polymers of component A are for example thermoplastic polymers such as polyolefins like polyethylene, polypropylene or copolymers thereof. The thermoplastic polymer is for example polypropylene.

Further examples for organic polymers (component A) are:
1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, for example polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EM), LLDPE/EVA, LLDPE/EAA and alternating or random polyal-kylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

Homopolymers and copolymers from 1.)–4.) may have any stereostructure including syndiotactic, isotactic, hemi-isotactic or atactic; for example atactic polymers. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; for example atactic polymers. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; for example atactic polymers. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates;

polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

19. Polycarbonates and polyester carbonates.

20. Polyketones.

21. Polysulfones, polyether sulfones and polyether ketones.

22. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

Component B is advantageously contained in the compositions of the invention in an amount from about 0.01 to about 20% by weight based on the polymeric substrate A; for example about 0.1 to about 10%, for example from about 0.25 to about 8% by weight; for instance from about 0.5 to about 3% by weight. For example about 0.05, 1, 1.5, 2, 3, 4 or 5 weight percent.

If a further conventional flame retardant is present in the compositions of this invention, it is advantageously contained in an amount from about 0.5 to about 45% by weight of the polymeric substrate A; for instance about 3 to about 40%; for example about 5 to about 35% by weight of component A.

The ratio (parts by weight) of the compounds of this invention to further conventional flame retardants is for example between about 1:5 to about 1:200, for instance from about 1:50 to about 1:100, or about 1:10 to about 1:25. For example the ratio of component B to further conventional flame retardants is from about 1:10 to about 1:200, from about 1:25 to about 1:200, from about 1:50 to about 1:200 or from about 1:100 to about 1:200. For example, the weight ratio of component B to further conventional flame retardants is from about 1:5 to about 1:100, from about 1:5 to about 1:50, from about 1:5 to about 1:25, or from about 1:5 to about 1:10.

The amount of the further conventional flame retardants employed also depends on the effectiveness of the specific compound(s), the polymer and the specific application type; for example, an amount of 5 to 15% by weight of the compound tris[3-bromo-2,2-bis(bromomethyl)propyl] phosphate may be as efficient as an amount of 30 to 45% by weight of the compound decabromodiphenyl oxide in respect of the flame retardancy of the final composition.

The resulting stabilized compositions of the invention may optionally also contain various conventional additives, for example in amounts from about 0.01 to about 10%, for instance from about 0.025 to about 4%, for example from about 0.1 to about 2% by weight of component A, such as the materials listed below, or mixtures thereof.

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl) phenol, 2,4-dimethyl-6-(1'-methylheptadec 1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octade-cyloxyphenol, 2,6-di-tert-butylhydroquinone, 2,5-di-tert-butyl-4-hydroxyanisole, 3,5-di-tert-butyl-4-hydroxyanisole, 3, 5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4- octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3, 5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O—, N— and S-benzyl compounds, for example 3,5, 3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3, 3-tetramethylbutyl)phenyl]-2,2-bis(3,5-di-tert-butyl-4-hydroxybenzyl)malonate.

1.9. Aromatic hydroxybenzyl compounds, for example 1,3, 5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis (octylmercapto)-6-(3,5-di-tert-butyl-4-hydroxyanilino)-1,3, 5-triazine, 2-octylmercapto-4,6-bis(3,5-di-tert-butyl-4-hydroxyanilino)-1,3,5-triazine, 2-octylmercapto-4,6-bis(3, 5-di-tert-butyl-4-hydroxyphenoxy)-1,3,5-triazine, 2,4,6-tris (3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris-(3,5-di-tert-butyl-4-hydroxyphenylethyl)-1,3,5-triazine, 1,3,5-tris(3,5-di-tert-butyl-4-hydroxy-phenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis-(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis (3,5-di-tert-butyl-4-hydroxy-phenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine; for example p,p'-di-tert-octyldiphenylamine, 4-n-butylaminophenol, 4-butyrylaminophenol, 4-nonanoylaminophenol, 4-dodecanoylaminophenol, 4-octa-decanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl- 2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α, α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxy-phenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$-]$_2$— where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]-benzotriazole; 2-[2'-hydroxy-3'-(1,1,3,3-tetramethylbutyl)-5'-(α,α-dimethylbenzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyidithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3, 5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1, 2,3,4-butane-tetracarboxylate, 1,1'-(1,2-ethanediyl)-bis(3,3, 5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2, 4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4, 6-trichloro-1,3,5-triazine as well as 4-butylamino-2,2,6,6-tetramethylpiperidine (CAS Reg. No. [136504–96–6]); N-(2,2,6,6-tetramethyl-4-piperidyl)-n-dodecylsuccinimid, N-(1,2,2,6,6-pentamethyl-4-piperidyl)-n- dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro[4,5]decane und epichlorohydrin, 1,1-bis(1,2,2,6,6-pentamethyl-4-piperidyloxycarbonyl)-2-(4-methoxyphenyl) ethene, N,N'-bis-formyl-N,N'-bis(2,2,6,6-tetramethyl-4-piperidyl)hexamethylenediamine, diester of 4-methoxy-methylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyl-oxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-1 2-methyl-dibenz[d,g]-1,3,2-dioxaphosphocin, 2,2',2''-nitrilo[triethyltris(3,3',5,5'-tetra-tert-butyl-1,1'-biphenyl-2,2'-diyl)phosphite], 2-ethylhexyl (3,3',5, 5'-tetra-tert-butyl-1,1 '-biphenyl-2,2'-diyl)phosphite, 5-butyl-5-ethyl-2-(2,4,6-tri-tert-butylphenoxy)-1,3,2-dioxaphosphirane.

Specific examples are the following phosphites:

Tris(2,4-di-tert-butylphenyl) phosphite (Irgafos®168, Ciba-Geigy), tris(nonylphenyl) phosphite,

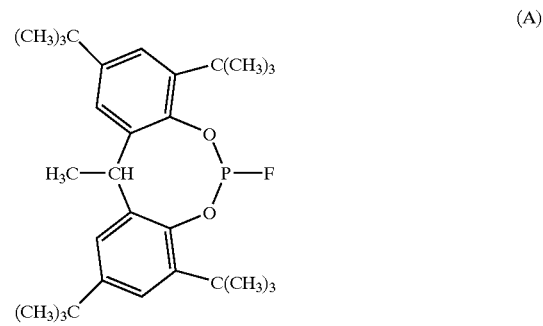

(A)

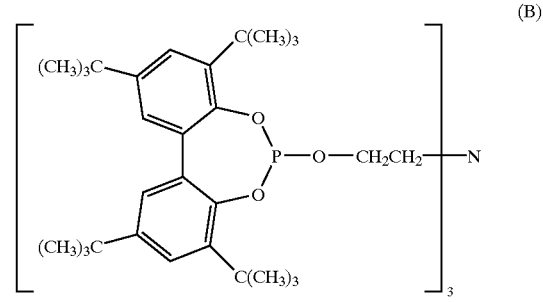

(B)

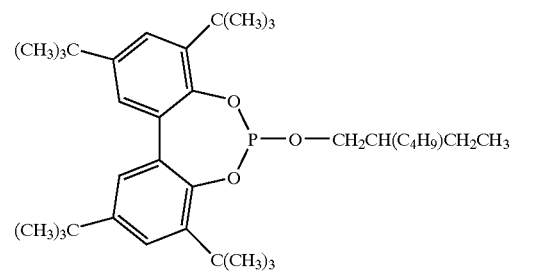

(C)

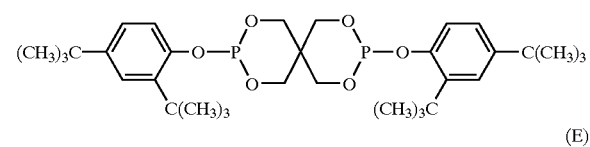

(D)

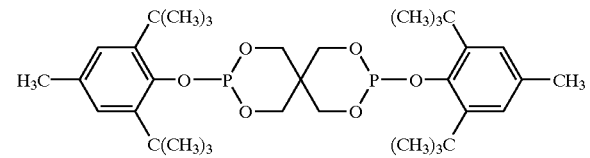

(E)

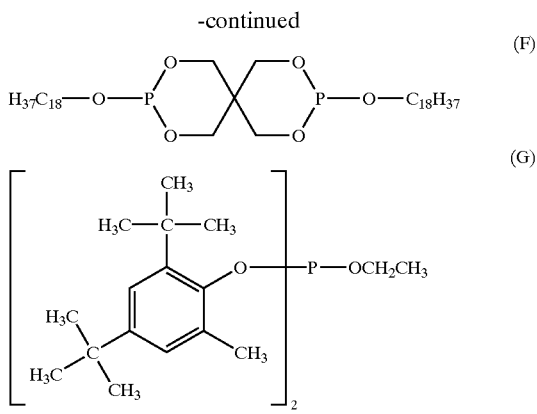

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercapto-benzimidazole, zinc dibutyidithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, for example, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers). Specific examples are 1,3:2,4-bis(3',4'-dimethylbenzylidene)sorbitol, 1,3:2,4-di(paramethyldibenzylidene) sorbitol, und 1,3:2,4-di(benzylidene)sorbitol.

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl] benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

15. Amine oxides, for example amine oxide derivatives as disclosed in U.S. Pat. Nos. 5,844,029 and 5,880,191, didecyl methyl amine oxide, tridecyl amine oxide, tridodecyl amine oxide and trihexadecyl amine oxide. U.S. Pat. Nos. 5,844,029 and 5,880,191 disclose the use of saturated hydrocarbon amine oxides towards the stabilization of thermoplastic resins. It is disclosed that the thermoplastic compositions may further contain a stabilizer or mixture of stabilizers selected from phenolic antioxidants, hindered amine light stabilizers, ultraviolet light absorbers, organic phosphorus compounds, alkaline metal salts of fatty acids and thiosynergists.

The compositions may also contain a further conventional flame retardant, for instance one or more conventional organohalogen, organophosphorus or melamine based flame retardants. For example:

Oganohalogen flame retardants are for example:
Chloroalkyl phosphate esters (ANTIBLAZE® AB-100, Albright & Wilson; FYROL® FR-2, Akzo Nobel),
polybrominated diphenyl oxide (DE-60F, Great Lakes Corp.),
decabromodiphenyl oxide (DBDPO; SAYTEX® 102E),
tris[3-bromo-2,2-bis(bromomethyl)propyl] phosphate (PB 370®, FMC Corp.),
bis(2,3-dibromopropyl ether) of bisphenol A (PE68),
brominated epoxy resin,
ethylene-bis(tetrabromophthalimide) (SAYTEX® BT-93),
bis(hexachlorocyclopentadieno)cyclooctane (DECLORANE PLUS®),
chlorinated paraffins,
1,2-bis(tribromophenoxy)ethane (FF680),
tetrabromo-bisphenol A (SAYTEX® RB100),
ethylene bis-(dibromo-norbornanedicarboximide) (SAYTEX® BN-451),
bis-(hexachlorocyclopentadieno) cyclooctane,
tris-(2,3-dibromopropyl)-isocyanurate, and
ethylene-bis-tetrabromophthalimide.

The organophophorus flame retardants are for example:
Tetraphenyl resorcinol diphosphite (FYROLFLEX® RDP, Akzo Nobel),
triphenyl phosphate,
ammonium polyphosphate (APP) or (HOSTAFLAM® AP750), resorcinol diphosphate oligomer (RDP),
phosphazene flame retardants and
ethylenediamine diphosphate (EDAP).

Melamine based flame retardants are for example:
melamine cyanurate, MELAPUR® MC,
melamine borate,
melamine phosphate, MELAPUR@ P 46,
melamine polyphosphate MELAPUR® 200 and
melamine pyrophosphate.

Specific examples of additives are phenolic antioxidants (item 1 of the list), further sterically hindered amines (item 2.6 of the list), light stabilizers of the benzotriazole and/or o-hydroxyphenyltriazine class (items 2.1 and 2.8 of the list), phosphites and phosphonites (item 4 of the list) and peroxide-destroying compounds (item 5.) of the list.

Additional specific examples of additives (stabilizers) which are benzofuran-2-ones, such as described, for example, in U.S. Pat. No. 4,325,863, U.S. Pat. No. 4,338,244 or U.S. Pat. No. 5,175,312.

The instant composition can additionally contain another UV absorber selected from the group consisting of the s-triazines, the oxanilides, the hydroxybenzophenones, benzoates and the (α-cyanoacrylates. Particularly, the instant composition may additionally contain an effective stabilizing amount of at least one other 2-hydroxyphenyl-2H-benzotriazole; another tris-aryl-s-triazine; or hindered amine or mixtures thereof. For example, additional components are selected from pigments, dyes, plasticizers, antioxidants, thixotropic agents, levelling assistants, basic costabilizers, further light stabilizers like UV absorbers and/or sterically hindered amines, metal passivators, metal oxides, organophosphorus compounds, hydroxylamines, and mixtures thereof, especially pigments, phenolic antioxidants, calcium stearate, zinc stearate, UV absorbers of the 2-(2'-hydroxyphenyl)benzotriazole and 2-(2-Hydroxyphenyl)-1,3,5-triazine classes, and sterically hindered amines.

The additives of the invention and optional further components may be added to the polymer material individually or mixed with one another. If desired, the individual components can be mixed with one another before incorporation into the polymer for example by dry blending, compaction or in the melt.

Conveniently, the additives of this invention and possibly further additives as described above may be dry blended and then extruded, for instance in a twin screw extruder at 180–220° C., with or without nitrogen atmosphere. The material thus obtained may be further processed according to known methods. The surface of the articles formed do not show any loss of gloss or any kind of roughness.

Further, the instant invention pertains to a process for imparting light stability and flame retardancy to an organic polymeric substrate, which process comprises adding to said polymeric substrate an effective flame retarding amount of at least one compound of formula

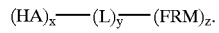

$(HA)_x\text{——}(L)_{\overline{y}}\text{——}(FRM)_z.$

The incorporation of the additives of the invention and optional further components into the polymer is carried out by known methods such as dry blending in the form of a powder, or wet mixing in the form of solutions, dispersions or suspensions for example in an inert solvent, water or oil. The additives of the invention and optional further additives may be incorporated, for example, before or after molding or also by applying the dissolved or dispersed additve or additive mixture to the polymer material, with or without subsequent evaporation of the solvent or the suspension/dispersion agent. They may be added directly into the processing apparatus (e.g. extruders, internal mixers, etc), e.g. as a dry mixture or powder or as solution or dispersion or suspension or melt.

The incorporation can be carried out in any heatable container equipped with a stirrer, e.g. in a closed apparatus such as a kneader, mixer or stirred vessel. The incorporation is for example carried out in an extruder or in a kneader. It is immaterial whether processing takes place in an inert atmosphere or in the presence of oxygen.

The addition of the additive or additive blend to the polymer can be carried out in all customary mixing machines in which the polymer is melted and mixed with the additives. Suitable machines are known to those skilled in the art. They are predominantly mixers, kneaders and extruders.

The process is for instance carried out in an extruder by introducing the additive during processing.

Specific examples of suitable processing machines are single-screw extruders, contrarotating and corotating twin-screw extruders, planetary-gear extruders, ring extruders or cokneaders. It is also possible to use processing machines provided with at least one gas removal compartment to which a vacuum can be applied.

Suitable extruders and kneaders are described, for example, in *Handbuch der Kunststoffextrusion, Vol. 1 Grundlagen*, Editors F. Hensen, W. Knappe, H. Potente, 1989, pp. 3–7, ISBN:3-446-14339-4 (*Vol. 2 Extrusionsanlagen* 1986, ISBN 3-446-14329-7).

For example, the screw length is 1–60 screw diameters, for example 35–48 screw diameters. The rotational speed of the screw is for instance 10–600 rotations per minute (rpm), for example 25–300 rpm.

The maximum throughput is dependent on the screw diameter, the rotational speed and the driving force. The process of the present invention can also be carried out at a level lower than maximum throughput by varying the parameters mentioned or employing weighing machines delivering dosage amounts.

If a plurality of components are added, these can be premixed or added individually.

The additives of the invention and optional further additives can also be sprayed onto the polymer material. They are able to dilute other additives (for example the conventional additives indicated above) or their melts so that they can be sprayed also together with these additives onto the material. Addition by spraying during the deactivation of the polymerization catalysts is particularly advantageous; in this case, the steam evolved may be used for deactivation of the catalyst. In the case of spherically polymerized polyolefins it may, for example, be advantageous to apply the additives of the invention, optionally together with other additives, by spraying.

The additives of the invention and optional further additives can also be added to the polymer in the form of a masterbatch ("concentrate") which contains the components in a concentration of, for example, about 1% to about 40%, for example about 2% to about 20% by weight incorporated in a polymer. The polymer must not be necessarily of identical structure than the polymer where the additives are added finally. In such operations, the polymer can be used in the form of powder, granules, solutions, suspensions or in the form of latices.

Incorporation can take place prior to or during the shaping operation. The materials containing the additives of the invention described herein are for example used for the production of molded articles, for example rotomolded articles, injection molded articles, profiles and the like. Thus, a molded polymer article made flame retardant by the incorporation of at least one compound of the formula

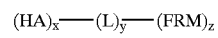

$(HA)_x\text{——}(L)_{\overline{y}}\text{——}(FRM)_z$ is another object of the invention.

It is also contemplated that PTFE, polytetrafluoroethylene (for example Teflone® 6C; E. I. Du Pont), may be advantageously added to the present compositions as an additional flame retardant, as disclosed in U.S. application Ser. No. 60/312,517, filed Aug. 15, 2001.

The effective flame retarding amount of component B is that needed to show flame retarding efficacy as measured by one of the standard methods used to assess flame retardancy. These include the NFPA 701 Standard Methods of Fire Tests for Flame-Resistant Textiles and Films, 1989 and 1996 editions; the UL 94 Test for Flammability of Plastic Materials for Parts in Devices and Appliances, 5th Edition, Oct. 29, 1996; Limiting Oxygen Index (LOI), ASTM D-2863; and Cone Calorimetry, ASTM E-1354. Ratings according to the UL 94 V test are as compiled in the following table:

| Rating | Afterflame time | Burning drips | Burn to Clamp |
|---|---|---|---|
| V-0 | <10 s | no | no |
| V-1 | <30 s | no | no |
| V-2 | <30 s | yes | no |
| Fail | <30 s | | yes |
| Fail | >30 s | | no |

Coadditives found particularly useful for use with the instant compounds in flame retardant compositions are as follows:

UV absorbers:

2-(2-hydroxy-3,5-di-α-cumylphenyl)-2H-benzotriazole, (TINUVIN® 234, Ciba Specialty Chemicals Corp.);

2-(2-hydroxy-5-methylphenyl)-2H-benzotriazole, (TINUVIN® P, Ciba Specialty Chemicals Corp.);

5-chloro-2-(2-hydroxy-3,5-di-tert-butylphenyl)-2H-benzotriazole, (TINUVIN® 327, Ciba Specialty Chemicals Corp.);

2-(2-hydroxy-3,5-di-tert-amylphenyl)-2H-benzotriazole, (TINUVIN® 328, Ciba Specialty Chemicals Corp.);

2-(2-hydroxy-3-α-cumyl-5-tert-octylphenyl)-2H-benzotriazole, (TINUVIN® 928, Ciba Specialty Chemicals Corp.);

2,4-di-tert-butylphenyl 3,5-di-tert-butyl-4-hydroxybenzoate, (TINUVIN® 120, Ciba Specialty Chemicals Corp.);

2-hydroxy-4-n-octyloxybenzophenone, (CHIMASSORB® 81, Ciba Specialty Chemicals Corp.);

2,4-bis(2,4-dimethyphenyl)-6-(2-hydroxy-4-octyloxyphenyl)-s-triazine, (CYASORB® 1164, Cytec).

The following examples are meant for illustrative purposes only and are not to be construed to limit the scope of this invention in any manner whatsoever. Where given, room temperature depicts a temperature in the range 20–25° C. Percentages are by weight of the polymer substrate unless otherwise indicated.

Test Methods

NFPA 701 Standard Methods of Fire Tests for Flame-Resistant Textiles and Films, 1989 and 1996 editions;

UL 94 Test for Flammability of Plastic Materials for Parts in Devices and Appliances, 5th Edition, Oct. 29, 1996;

Limiting Oxygen Index (LOI), ASTM D-2863;

Cone Calorimetry, ASTM E-1 or ASTM E 1354;

ASTM D 2633–82, burn test.

Compound Preparation Examples

EXAMPLE P1

Preparation of Compound 126

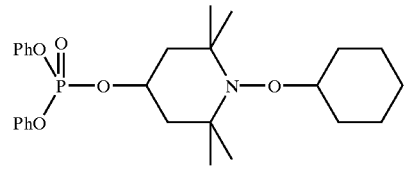

Compound 126

A mixture of 25 g 4-hydroxy-2,2,6,6-tetramethylpiperidine-1-cyclohexyloxy (0.098 mol), 40 mL triethylamine (0.29 mol), and 0.5 g dimethylaminopyridine in 80 mL methylene chloride is cooled to 0C under nitrogen flow. A solution of 23 mL diphenyl chlorophosphate (0.11 mol) is added dropwise over 30 minutes. The mixture is allowed to warm to room temperature and is stirred 17 hours. The mixture is concentrated; a 10% ethyl acetate in heptane solution and a 1 N HCl solution are added. The aqueous layer is separated and extracted with 10% ethyl acetate in heptane solution. The organic layers are washed with 1 N HCl, water, and sat. $NaHCO_3$ solution, dried over $MgSO_4$, and concentrated. The oil is purified by column chromatography using heptane and ethyl acetate solvents on silica gel to give 41.5 g (87% yield) of a pale yellow oil. $^1$H NMR δ 7.38–7.29 (m), 7.26–7.15 (m), 4.85–4.72 (m), 3.62–3.51 (m), 2.06–1.87 (m), 1.78–1.63 (m), 1.56–1.48 (m), 1.28–1.10 (m), 1.17 (s), 1.14 (s). $^{31}$P NMR δ–11.89.

EXAMPLE P2

Preparation of Compound 012

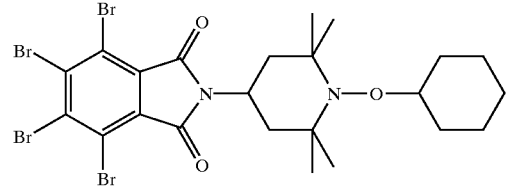

Compound 012

A mixture of 24.2 g tetrabromophthalic anhydride (0.062 mol) in 75 mL acetic acid and 180 mL toluene is heated to reflux, and a solution of 16 g 1-(cyclohexyloxy)-2,2,6,6-tetramethyl-4-piperidinamine (see U.S. Pat. No. 5,204,473) in toluene (40 mL) is added. A Dean-Stark trap is attached to the reaction flask. The mixture is refluxed 11.5 hours. The reaction is allowed to cool and the solvents are removed in vacuo. The residue is recrystallized in acetic acid and toluene to give 36.3 g white solid (82% yield.) $^1$H NMR δ 4.59 (tt), 3.63 (m), 2.51 (t), 2.14–1.06 (m). $^{13}$C NMR δ 163.8, 137.4, 130.3, 121.2, 81.9, 60.0, 44.9, 41.8, 34.3, 34.3, 25.9, 25.0, 20.4.

EXAMPLE P3

Preparation of Compound 137

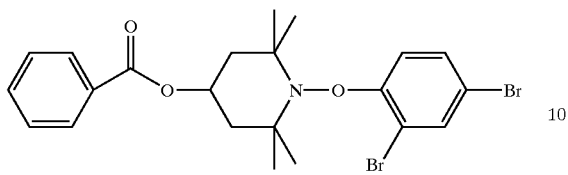
Compound 137

A mixture of 5 g 4-hydroxy-2,2,6,6-tetramethylpiperidine-1-oxyl benzoate (0.018 mol), 9.9 mL t-butyl nitrite (0.083 mol), and 1.8mg copper (II) fluoride (0.018 mmol, 0.1 mol %) in 180 mL pyridine is heated to 65–70C under nitrogen. A solution of 13.6 g 2,4-dibromoaniline (0.054 mol) in 20 mL pyridine is added slowly over a period of 45 minutes. The mixture is stirred 15 more minutes at 70° C., and is stirred a further three days at room temperature. The solvent is removed in vacuo; the residue is purified by column chromatography using heptane and ethyl acetate solvents on silica gel followed by recrystallization in diethyl ether and heptane to give 5 g white crystals (55% yield.) $^1$H NMR δ 8.04(d), 7.60 (d), 7.58 (t), 7.46 (t), 7.45 (d), 7.31 (dd), 5.40 (tt), 2.14 (d), 1.87 (t), 1.47 (s), 1.07 (s).

EXAMPLE P4

Preparation of Compound 040

Compound 040

A solution of 3,9-dichloro-2,4,8,10-tetraoxo-3,9-diphosphaspiro[5.5]undecane (see U.S. Pat. No. 4,070,336) (35 g, 0.13 mmol) and triethylamine (56 mL, 0.40 mol) in toluene (200 mL) is cooled to 0C under nitrogen. A solution of 4-hydroxy-2,2,6,6-tetramethylpiperidine-1-oxyl (60.2 g, 0.24 mol) in toluene (200 mL) is added dropwise. The mixture is stirred 18 hours at room temperature, and the solvents are evaporated. The residue is taken up in water and $CH_2Cl_2$. The aqueous layer is separated and extracted several times with $CH_2Cl_2$. The organic layers are dried over $MgSO_4$ and concentrated, and the residue is recrystallized with heptane to give 64.0 g white solid (78% yield.) To the product is added 350 mL toluene, and trace remaining acid is neutralized using concentrated ammonium hydroxide. The mixture is cooled to 0C under nitrogen. A 70% solution of t-butylhydroperoxide in water (28 mL, 0.20 mol) is extracted into heptane; the heptane is dried over $MgSO_4$, filtered, and added dropwise to the toluene mixture. The mixture is stirred 18 hours at room temperature; the product is isolated by filtration to give 56.9 g white solid (84% yield.) $^1$H NMR δ 4.74(m), 4.64 (ddd), 4.30 (dd), 4.00–4.70 (m), 3.59 (m), 2.00 (b), 1.70 (b), 1.00–2.10 (m). $^{31}$P NMR δ–7.86.

EXAMPLE P5

The following compounds are prepared:

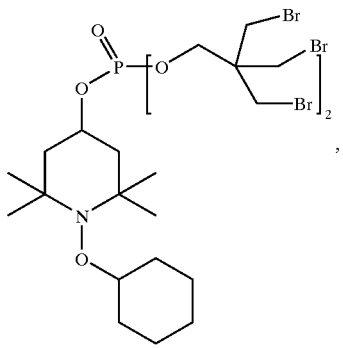

,

-continued

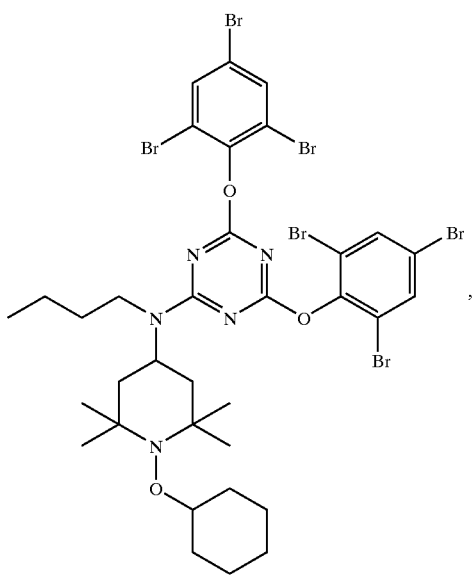

,

-continued

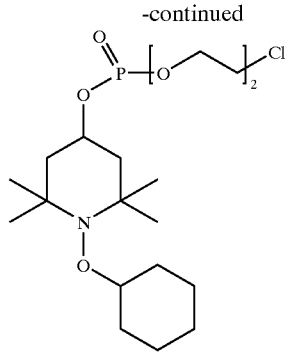

,

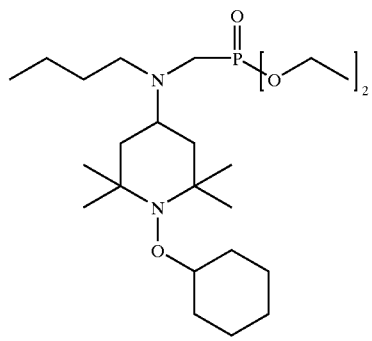

and

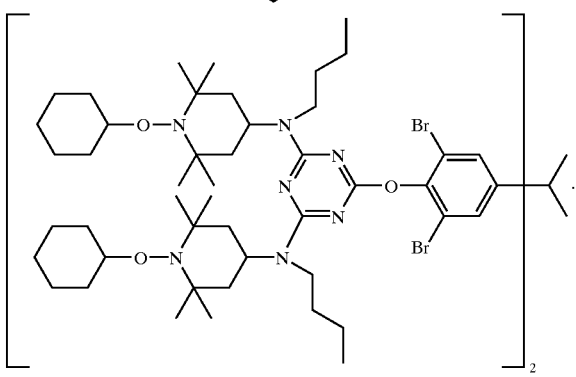

EXAMPLE P6

A copolymer of

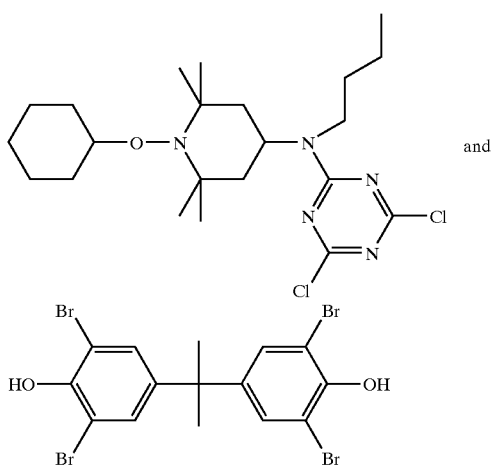

and is prepared.

EXAMPLE P7

Compounds of Examples P1, P2, P4–P6, are prepared, replacing the cyclohexyloxy group of the hindered amine with n-propoxy, hydroxy, 2-methyl-2hydroxypropoxy and oxyl.

Application Examples

EXAMPLE A1

Fiber grade polypropylene is dry blended with the additives of the table below. Each additive is 1% by weight based on the weight of the polypropylene. Each of the polypropylene formulations is compounded in a twin screw extruder and the fibers are extruded using a Hills fiber extruder. Compounding is carried out at 425° F. The fiber extrusion is carried at 475° F. and 525° F. Socks are knitted from the fibers and are evaluated for flame retardant efficacy using the NFPA 701 test.

|  | Fiber ext. temp (° F.) | Drip Burn (seconds) |
| --- | --- | --- |
| Blank | 475 | >100 |
| Blank | 525 | >100 |
| 1% Compound 040 | 475 | 2.31 |
| 1% Compound 137 | 525 | 12.79 |
| 1% Compound 126 | 475 | 0.6 |

The shorter the drip burn time, the more flame retardant the formulationis. It is seen that the compounds of the present invention provide significant flame retardancy to polypropylene fibers.

EXAMPLE A2

Molding grade polypropylene (Profax® 6501; Montell) is dry blended with the test additives and then melt compounded in a twin screw extruder at 220° C. Base stabilization is 500 ppm N,N-di(alkyl)hydroxylamine produced by the direct oxidation of N,N-di(hydrogenated tallow)amine (Irgastab® FS-042) and 500 ppm calcium stearate. Plaques (125 mil) are prepared by injection molding from the formulations using a Boy Injection Molder at 475° F. (246° C.). The specimens are tested for flame retardancy according to the UL-94 vertical burn test specifications.

The present additives of Examples P1–P7 provide significant flame retardancy.

EXAMPLE A3

Polyethylene fibers are prepared from fiber grade polyethylene by dry blending with test additives and melt compounding at 400° F. Fibers are extruded from this formulation using a Hills laboratory scale fiber extruder. Socks are knitted from the fibers and are tested for flame retardancy according to NFPA 701 vertical burn method. Polyethylene fibers contain 0.5%, 1% or 2% of an additive of present compounds P1-P7. These formulated fibers are tested for flame retardancy according to NFPA 701.

The fibers containing an additive of Examples P1–P7 of the present invention exhibit enhanced flame retardancy.

EXAMPLE A4

Molding grade polypropylene (Profax® 6501; Montell) is dry blended with the test additives of this invention and then melt compounded in a twin screw extruder at 200° C. under nitrogen. Base stabilization is 500 ppm N,N-di(alkyl) hydroxylamine produced by the direct oxidation of N,N-di (hydrogenated tallow)amine (Irgastab® FS-042) and 500 ppm calcium stearate. Plaques (125 mil) are prepared by injection molding from the formulations using a Boy Injection Molder at 475° F. (246° C.). The specimens are tested for flame retardancy according to the UL-94 vertical burn test specifications.

The plaques are tested for flame retardancy by the UL 94V thick section test. The ratings achievable are V-0 (best rating), V-1, and V-2. Additive levels are reported in weight percent based on the total composition.

The results show that the requirements of the V-0 rating in the UL-94 vertical burning test are only met by the composition of present invention.

EXAMPLE A5

Foam grade polyethylene is dry blended with test additives and then melt compounded into pellets. The pelletized fully formulated resin is then blown into foam.

The polyethylene foam prepared contains an instant additive of Examples P1–P7. The formulated foam is tested for flame retardancy according to the UL-94 burn test method.

The foam containing an additive of present Examples P1–P7 exhibit excellent flame retardancy.

EXAMPLE A6

Wire & cable grade polyethylene is dry blended with test additives and then melt compounded into pellets. The pelletized fully formulated resin is then extruded onto wire.

Test specimens are tested for flame retardancy using the ASTM D 2633-82 burn test conditions. The formulations containing a compound of the present invention of Examples P1–P7 exhibit enhanced flame retardancy.

EXAMPLE A7

Fiber grade polyethylene is dry-blended with test additives of present Examples P1–P7. Non-woven fabrics are produced from the polymer blend formulations by a spun-bonded or melt-blown process.

The non-woven fabrics made thereby are tested for flame retardancy according to the NFPA 701 vertical burn test specifications. The fabrics containing the present compounds of Examples P1–P7 exhibit excellent flame retardancy.

EXAMPLE A8

Fiber grade polypropylene is dry-blended with test additives of Examples P1–P7. Non-woven fabrics are produced from the polymer blend formulations by a spun-bonded or melt-blown process.

The non-woven fabrics made thereby are tested for flame retardancy according to the NFPA 701 vertical burn test specifications. The fabrics containing an additive selected from present Examples P1–P7 exhibit excellent flame retardancy.

EXAMPLE A9

Molding grade polystyrene is dry-blended with test additives of present Examples P1–P7 and then melt compounded. Specimens are injection molded from these test formulations.

The specimens are tested for flame retardancy according to the UL-94 burn test specifications. The molded specimens containing the present compounds of Examples P1–P7 exhibit excellent flame retardancy.

EXAMPLE A10

Foam grade polystyrene is dry-blended with test additives of Examples P1–P7 and then melt compounded. Foam polystyrene specimens are prepared from these test formulations.

The specimens are tested for flame retardancy according to the UL-94 burn test specifications. The foam specimens containing the present compounds of Examples P1–P7 exhibit excellent flame retardancy.

EXAMPLE A11

Molding grade ABS is dry blended with the an additive selected from present Examples P1–P7, then melt compounded at 425° F. (218° C.). Specimens 125 mil (⅛") thick are then injection molded from this formulation using a Boy Injection Molder at 450° F. (232° C.). The specimens are tested for flame retardancy according to the UL-94 vertical burn test specifications.

The specimens containing the present compounds selected from Examples P1–P7 exhibit excellent flame retardancy.

EXAMPLE A12

Fiber grade polypropylene is dry blended with an additive selected from the present Examples P1–P7, and then melt compounded at 234° C. (450° F.) into pellets. The pelletized fully formulated resin is then spun at 246° C. (475° F.) into fiber using a Hills laboratory model fiber extruder. The spun tow of 41 filaments is stretched at a ratio of 1:3.2 to give a final denier of 615/41.

Socks are knitted from the stabilized polypropylene fiber on a Lawson-Hemphill Analysis Knitter and tested under NFPA 701 vertical burn procedure. The time in seconds for the knitted sock to extinguish after the insult flame is removed is reported as "After Flame". Both the maximum time for any one replicate and the total time for ten replicates are measured. Efficacy as a flame retardant is demonstrated when low After Flame times are observed relative to a blank sample containing no flame retardant.

The specimens containing the present compounds selected from Examples P1-P7 exhibit excellent flame retardancy.

EXAMPLE A13

Film grade polyethylene is dry blended with the with an additive selected from the present Examples P1–P7, and then melt compounded into pellets. The pelletized fully formulated resin is then blown at 205° C. using a MPM Superior Blown film extruder.

The films are tested for flame retardancy under NFPA 701 test conditions. The specimens containing the present compounds selected from Examples P1–P7 exhibit excellent flame retardancy.

Film grade polypropylene is handled in a similar fashion and polypropylene films containing the instant compounds also show flame retardancy.

EXAMPLE A14

Molded test specimens are prepared by injection molding thermoplastic olefin (TPO) pellets containing a present test compound selected from compounds of Examples P1–P7. The TPO formulations may also contain a pigment, a phosphite, a phenolic antioxidant or hydroxylamine, a metal stearate, a UV absorber or a hindered amine stabilizer or a mixture of hindered amine and UV absorber.

Pigmented TPO formulation composed of polypropylene blended with a rubber modifier where the rubber modifier is an in-situ reacted copolymer or blended product containing copolymers of propylene and ethylene with or without a ternary component such as ethylidene norbornene are stabilized with a base stabilization system consisting of an N,N-dialkylhydroxylamine or a mixture of hindered phenolic antioxidant and an organophosphorus compound.

The TPO plaques are tested for flame retardancy using the UL-94 Vertical Burn conditions. A minimum of three replicates are tested. Efficacy as a flame retardant is measured relative to a blank sample containing no flame retardant.

The specimens containing the present compounds of Examples P1–P7 exhibit excellent flame retardancy.

EXAMPLE A15

Film grade ethylene/vinyl acetate (EVA) copolymers containing 20 weight percent or less of vinyl acetate are dry blended with test additives and then melt compounded into pellets. The pelletized fully formulated resin is then blown into a film at 205° C. using a MPM Superior Blown-film extruder.

The films are tested for flame retardancy under NFPA 701 test conditions. The films containing the present compounds selected from Examples P1–P7 exhibit excellent flame retardancy.

Film grade low density polyethylene (LDPE) which contains some linear low density polyethylene (LLDPE) and/or ethylene/vinyl acetate (EVA) are dry blended with test additives and blown into film as described above for EVA copolymer resin. The films are tested for flame retardancy under NFPA 701 test conditions and those containing the present compounds selected from Examples P1–P7 exhibit excellent flame retardancy.

EXAMPLE A16

High impact polystyrene (HIPS) polymer (STYRON® 484C, Dow Chemical Co.) is compounded with a present compound of Examples P1–P7, pelletized and then injection or compression molded into plaques. These plaques are tested for flame retardant efficacy using cone calorimetry, LOI or UL-94 test method.

The plaques containing an instant compound of Examples P1–P7, exhibit excellent flame retardancy. Flame retardant HIPS polymers find application in housings for business machines.

EXAMPLE A17

This Example shows the efficacy of the present compounds in PVC formulations. Such formulations are useful in flexible or rigid PVC and in wire and cable applications.

Typical formulations are seen below:

| Component | parts | parts | parts | parts |
|---|---|---|---|---|
| PVC resin | 100 | 100 | 100 | 100 |
| tin mercaptide | 1.5 | — | 2.0 | — |
| tin carboxyate | — | 2.5 | — | 2.0 |
| process aid | 1.5 | 1.5 | 2.0 | 2.0 |
| impact mod. | 6.0 | 6.0 | 7.0 | 7.0 |
| paraffin wax | 1.0 | 0.3 | 1.0 | 1.0 |
| polyethyl wax | 0.1 | 0.1 | 0.2 | 0.2 |
| Ca stearate | 1.0 | — | 0.8 | — |
| pigment | 1.0 | 0.9 | 5.0 | 5.0 |

Fully formulated PVC containing one of the present compounds of Examples P1–P7 is pelletized and then injection molded into test plaques for examination of flame retardancy using the UL-94 or LOI test method.

The PVC plaques containing the instant compounds of Examples P1–P7 demonstrate excellent flame retardancy.

EXAMPLE A18

Fiber grade poly(ethylene terephthalate) (PET) is dry blended with a test additive of Examples P1–P7, then melt compounded at 550° F. and then pelletized. The polyester pellets are dried at 175° F. for 24 hours under vacuum. The dried pellets are extruded into fibers using a Hills laboratory scale fiber extruder at 550° F. Socks are knitted from these fibers and tested for flame retardancy according to NFPA 701 test method.

The fibers containing a present compound of Examples P1–P7, exhibit enhanced flame retardancy.

EXAMPLE A19

Thermoplastic resins including polypropylene, polyethylene homopolymer, polyolefin copolymer or thermoplastic olefins (TPO), high impact polystyrene (HIPS) and ABS are dry blended with an instant compound of Examples P1–P7, and then melt compounded into pellets. The pelletized fully formulated resin is then processed into a useful article such as extrusion into fiber; blown or cast extrusion into film; blow molded into bottles; injection molded into molded articles, thermoformed into molded articles, extruded into wire and cable housing or rotation molded into hollow articles.

The articles containing the instant compounds of Examples P1–P7 exhibit flame retardancy when tested by a known standard test method.

Polyethylene wire and cable applications are tested for flame retardancy according to ASTM D-2633–82 burn test method. The materials containing the instant compounds of Examples P1–P7 show excellent flame retardancy.

EXAMPLE A20

Articles prepared according to Example A19 which additionally contain an organophosphorus stabilizer selected from the group consisting of tris(2,4-di-tert-butylphenyl) phosphite, bis(2,4-di-tert-butyl-6-methylphenyl) ethyl phosphite, 2,2',2"-nitrilo[triethyl-tris-(3,3',5,5'-tetra-tert-butyl-1,1'-biphenyl-2,2'-diyl) phosphite], tetrakis(2,4-di-butylphenyl) 4,4'-biphenylenediphonite, tris(nonylphenyl) phosphite, bis(2,4-di-tert-butylphenyl) pentaerythrityl diphosphite, 2,2'-ethylidenebis(2,4-di-tert-butylphenyl) fluorophosphite and 2-butyl-2-ethylpropan-1,3-diyl 2,4,6-tri-tert-butylphenyl phosphite exhibit good flame retardancy properties.

EXAMPLE A21

Articles prepared according to Example A19 which additionally contain a o-hydroxyphenyl-2H-benzotriazole, a hydroxyphenyl benzophenone or a o-hydroxyphenyl-s-triazine UV absorber selected from the group consisting of 2-(2-hydroxy-3,5-di-α-cumylphenyl)-2H-benzotriazole, 2-(2-hydroxy-5-methylphenyl)-2H-benzotriazole, 5-chloro-2-(2-hydroxy-3,5-di-tert-butylphenyl)-2H-benzotriazole, 2-(2-hydroxy-3,5-di-tert-amylphenyl)-2H-benzotriazole, 2-(2-hydroxy-3-α-cumyl-5-tert-octylphenyl)-2H-benzotriazole, 2,4-di-tert-butylphenyl 3,5-di-tert-butyl4-hydroxybenzoate, 2-hydroxy-4-n-octyloxybenzophenone and 2,4-bis(2,4-dimethyphenyl)-6-(2-hydroxy-4-octyloxyphenyl)-s-triazine exhibit good flame retardancy.

EXAMPLE A22

Articles prepared according to Example A19 which additionally contain a o-hydroxyphenyl-2H-benzotriazole, a hydroxyphenyl benzophenone or a o-hydroxyphenyl-s-triazine UV absorber selected from the group consisting of 2-(2-hydroxy-3,5-di-α-cumylphenyl)-2H-benzotriazole, 2-(2-hydroxy-5-methylphenyl)-2H-benzotriazole, 5-chloro-2-(2-hydroxy-3,5-di-tert-butylphenyl)-2H-benzotriazole, 2-(2-hydroxy-3,5-di-tert-amylphenyl)-2H-benzotriazole, 2-(2-hydroxy-3-α-cumyl-5-tert-octylphenyl)-2H- benzotriazole, 2,4-di-tert-butylphenyl 3,5-di-tert-butyl4-hydroxybenzoate, 2-hydroxy-4-n-octyloxybenzophenone and 2,4-bis(2,4-dimethyphenyl)-6-(2-hydroxy-4-octyloxyphenyl)-s-triazine exhibit good flame retardancy properties.

EXAMPLE A23

Examples A1–A22 are repeated with the co-use of a traditional halogenated flame retardant. The halogenated flame retardant is selected from decabromodiphenyl oxide (DBDPO; SAYTEX® 102E),
tris[3-bromo-2,2-bis(bromomethyl)propyl] phosphate (PB 370®, FMC Corp.),
bis(2,3-dibromopropyl ether) of bisphenol A (PE68),
ethylene-bis(tetrabromophthalimide) (SAYTEX® BT-93),
1,2-bis(tribromophenoxy)ethane (FF680),
tetrabromo-bisphenol A (SAYTEX® RB100),
ethylene bis-(dibromo-norbornanedicacboximide) (SAYTEX® BN-451), or
tris-(2,3-dibromopropyl)-isocyanurate.
Excellent results are achieved.

What is claimed is:

1. A compound of formula I

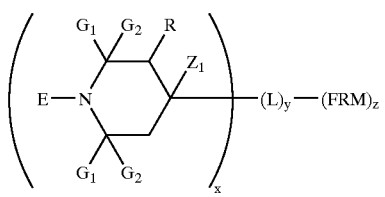

where
R is hydrogen or methyl,
$G_1$ and $G_2$ are independently alkyl of 1 to 4 carbon atoms or are together pentamethylene,
x, y and z are each independently greater than or equal to 1,
L is independently of each other a direct bond or a hydrocarbylene group,
$Z_1$ is hydrogen or hydrocarbyl or —$OR_1$, —$OCOR_1$, —$COOR_1$, —$CONR_1R_2$, —$NR_1COR_2$, —$COR_1$ or —$NR_1R_2$,
$R_1$ and $R_2$ are independently of each other hydrogen or hydrocarbyl, or $R_1$ and $R_2$ together form a hydrocarbylene group,
E is oxyl, hydroxyl, alkoxy, cycloalkoxy, aralkoxy, aryloxy, —O—CO—OG, —O—Si(G)$_3$, or —O—CH$_2$-OG where G is selected from the group consisting of hydrogen, an aliphatic, araliphatic and aromatic moiety; or E is —O—T—(OH)$_b$,
T is a straight or branched chain alkylene of 1 to 18 carbon atoms, cycloalkylene of 5 to 18 carbon atoms, cycloalkenylene of 5 to 18 carbon atoms, a straight or branched chain alkylene of 1 to 4 carbon atoms substituted by phenyl or by phenyl substituted by one or two alkyl groups of 1 to 4 carbon atoms,
b is 1, 2 or 3 with the proviso that b cannot exceed the number of carbon atoms in T, and when b is 2 or 3, each hydroxyl group is attached to a different carbon atoms of T, and FRM is independently of each other flame retardant moiety

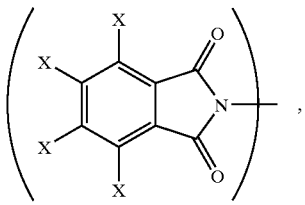

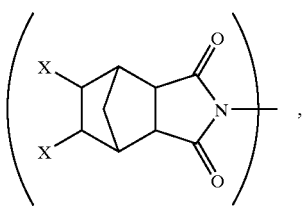

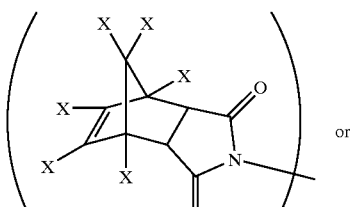

or

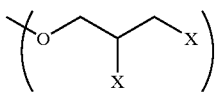

where X is chlorine or bromine.

2. A compound according to claim 1 in which E is oxyl, hydroxyl, methoxy, propoxy, cyclohexyloxy or octyloxy.

3. A compound according to claim 1 in which L is a direct bond.

4. A compound according to claim 1 that comprises a sterically hindered hydrocarbyloxyamine moiety selected from the group consisting of

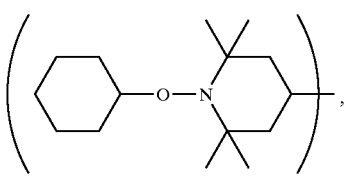

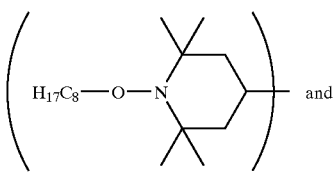

and

-continued
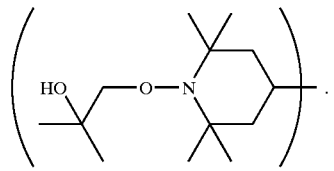
5. A compound according to claim 1 of formula
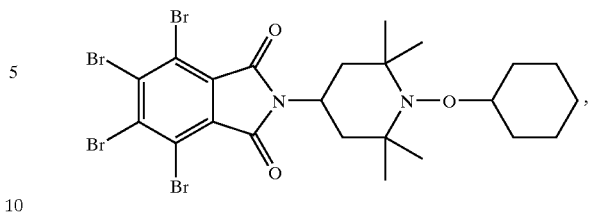
* * * * *